(12) United States Patent
Tsuchida et al.

(10) Patent No.: US 6,864,094 B2
(45) Date of Patent: Mar. 8, 2005

(54) METHOD OF PRESERVING OXYGEN INFUSIONS

(75) Inventors: Eishun Tsuchida, Tokyo (JP); Hiromi Sakai, Tokyo (JP); Kenichi Tomiyama, Tokyo (JP); Shinji Takeoka, Tokyo (JP); Keitaro Sou, Tokyo (JP)

(73) Assignee: Japan Science and Technology Corporation, Kawaguchi (JP)

( * ) Notice: Subject to any disclaimer, the term of this patent is extended or adjusted under 35 U.S.C. 154(b) by 47 days.

(21) Appl. No.: 10/091,440

(22) Filed: Mar. 7, 2002

(65) Prior Publication Data

US 2002/0137221 A1 Sep. 26, 2002

Related U.S. Application Data

(63) Continuation-in-part of application No. PCT/JP00/05512, filed on Aug. 17, 2000.

(30) Foreign Application Priority Data

Sep. 7, 1999 (JP) ............................................. 11-253119

(51) Int. Cl.[7] .............................................. G01N 33/72
(52) U.S. Cl. .............................. 436/66; 436/9; 436/127; 436/136; 436/174; 436/176
(58) Field of Search ........................... 436/8, 9, 15, 66, 436/127, 136, 174, 176; 435/2

(56) References Cited

U.S. PATENT DOCUMENTS

| | | | | |
|---|---|---|---|---|
| 4,776,991 A | * | 10/1988 | Farmer et al. ................ | 264/4.3 |
| 4,911,929 A | * | 3/1990 | Farmer et al. ............... | 424/450 |
| 5,234,903 A | * | 8/1993 | Nho et al. ...................... | 514/6 |
| 5,386,014 A | * | 1/1995 | Nho et al. .................... | 530/385 |
| 5,814,601 A | * | 9/1998 | Winslow et al. ............... | 514/6 |

FOREIGN PATENT DOCUMENTS

| | | |
|---|---|---|
| JP | 60-99820 | 6/1985 |
| JP | 63-218075 | 9/1988 |
| JP | 3-142231 | 6/1991 |
| JP | 4-5242 | * 1/1992 |
| JP | 4-26629 | 1/1992 |
| JP | 04-059735 | 2/1992 |
| JP | 4-503676 | 7/1992 |
| JP | 7-20857 | 3/1995 |
| JP | 7-246328 | 9/1995 |
| JP | 8-104649 | 4/1996 |
| JP | 08-301873 | 11/1996 |
| WO | WO 89/06969 A1 | 8/1989 |
| WO | WO 92/02239 A1 | 2/1992 |
| WO | WO 92/08478 A1 | 5/1992 |
| WO | WO 94/26286 A1 | 11/1994 |
| WO | WO 96/34889 A1 | 11/1996 |

OTHER PUBLICATIONS

Sakai et al. Bioconjugate Chemistry, vol. 11, Apr. 21, 2000, pp. 425–432.*
Sakai et al. Abstract from Jinko Ketsueki, vol. 7, No. 4, 1999, pp. 105–110.*
Federation Proceedings vol. 36, No. 1561, p. 567 (1977).
Hasegawa et al, *Biochem. Biophys, Res. Commun.*, vol. 105, pp. 1416–1419 (1982).
Tsuchida et al, *Bioconjugate Chem.*, vol. 8, pp. 534–538 (1997).
Sakai et al, *Bull. Chem. Soc. Jpn.*, vol. 67, pp. 1120–1125 (1994).
Takeoka et al, *Bioconjugate Chem.*, vol. 8, pp. 539–544 (1997).
Satoh et al, *ASAIO Journal*, vol. 38, M580–M584 (1992).
Wang et al, *Polymers Adv. Technol.*, vol. 3, pp. 17–21 (1992).
Sakai et al, *Bioconjugate Chem.*, vol. 8, pp. 23–30 (1997).
Sakai et al, *Biotechnol. Prog.*, vol. 12, pp. 119–125 (1996).
Komatsu et al, *Chemistry Letters*, vol. 1992, pp. 1325–1328 (1992).
The Society of Blood Substitutes, Japan, vol. 7, No. 3, p. 56, "Artificial Blood", Aug. 20, 1999.
Published Japanese Patent No. 2709419.

* cited by examiner

*Primary Examiner*—Maureen M. Wallenhorst
(74) *Attorney, Agent, or Firm*—Oblon, Spivak, McClelland, Maier & Neustadt, P.C.

(57) ABSTRACT

The present invention provides a method for preserving an oxygen infusion containing an aqueous suspension of molecular assemblies which contain hemoglobin or a heme compound, by:

a) modifying the molecular assemblies with polyoxyethylene; and
b) converting the hemoglobin or the heme compound into a deoxy-form by removing oxygen from the suspension.

28 Claims, 1 Drawing Sheet

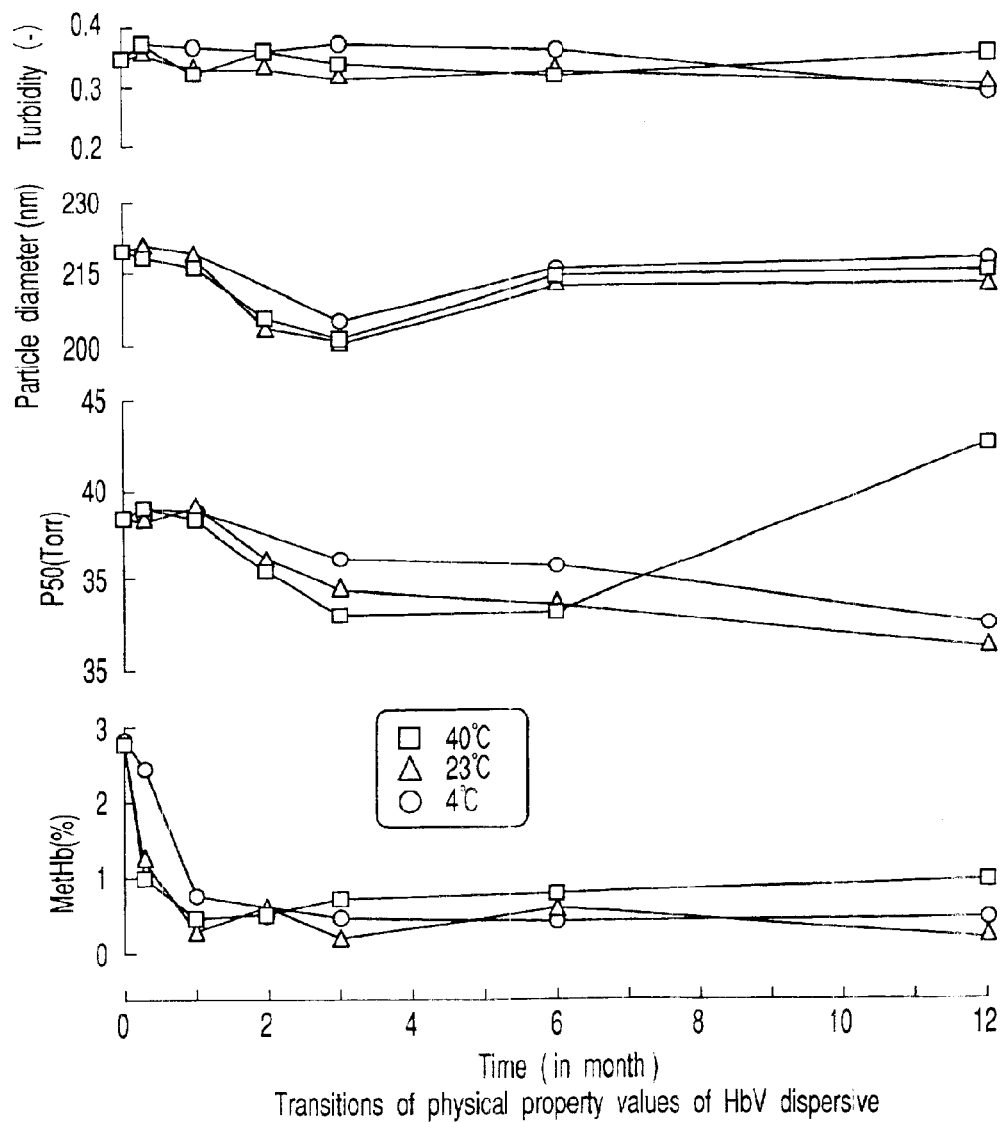
Transitions of physical property values of HbV dispersive
FIGURE

METHOD OF PRESERVING OXYGEN INFUSIONS

CROSS REFERENCE TO RELATED APPLICATIONS

This application is a Continuation-in-part (CIP) of International application No. PCT/JP00/05512 Filed on Aug. 17, 2000.

This application is based upon and claims the benefit of priority from prior Japanese Patent Application No. 11-253119, filed Sep. 7, 1999, the entire contents of which are incorporated herein by reference.

BACKGROUND OF THE INVENTION

1. Field of the Invention

The present invention relates to a method of stably preserving an oxygen infusion over a long period of time, as well as a method of manufacturing an oxygen infusion exhibiting a stable preservation over a long period of time.

The oxygen infusion of the present invention is widely applicable in the fields of medicine as well as pharmacy, for example. The present oxygen infusion can, for whole blood transfusion, be used as it is, or with some additives if necessary, in clinical therapies as a substitute for erythrocytes.

2. Description of the Background

Conventional blood transfusion systems which infuse human blood into a blood vessel exhibit various problems including blood type incompatibility, possibility of infection (hepatitis, HIV and the like) and an inadequate shelf-life of erythrocytes which is, i.e., only about 3 weeks. Hence, there has been a great demand for a substitute which can overcome these problems. As one such substitute, an infusion such as an electrolyte infusion and a colloidal infusion are noted, which are widely used at present.

However, these infusions do not exhibit the most essential function of blood, which is, an oxygen-carrying capability, and therefore it is of a great importance to develop an oxygen infusion, i.e., artificial red cells, which can substitute for the oxygen-carrying function of the erythrocyte. Some artificial oxygen infusions have been developed and clinical tests for such oxygen infusions have been advanced. Examples of the oxygen infusions include an aqueous suspension of a perfluorocarbon derivative having high oxygen solubility, a hemoglobin having reversible oxygen bonding ability, such as human hemoglobin, bovine hemoglobin or genetically-engineered hemoglobin; an intra-molecular cross-linked hemoglobin; a water-soluble high-molecular conjugated hemoglobin; and an inter-molecular cross-linked macromolecular hemoglobin. At the same time, however, it has become clear that various types of side effects arise due to the non-cellular structure of these artificial oxygen infusions.

The following are possible reasons why hemoglobin, referred to as Hb hereinafter, is inherently contained in the membranes of erythrocytes.

That is:

1) To suppress the influence of high viscosity and/or colloidal osmotic pressure due to a high-concentration Hb solution having a concentration of 12 to 15 g/dl;
2) To seal Hb having high physiological activity within a membrane, thereby suppressing the escape of hemoglobin;
3) To retain each type of phosphoric acid and glycolysis/reduction enzymes, which are used for maintaining the Hb functions, within the same reaction system; and
4) To obtain an advantage of the cell suspension system, which is non-Newtonian fluid exhibiting a characteristic physiological activity within the blood circulatory system (especially, peripheral blood vessels) due to distinctive fluidity thereof.

Considering the above-described inherent roles of the erythrocyte structure, it is clear that a suspension system of particles encapsulating hemoglobin therein is preferred as the oxygen infusion.

It is currently known that phospholipids, a component of living organisms, form an vesicle structure by themselves, and Djordjevich and Miller have begun studies of hemoglobin vesicles which utilize liposomes made of phospholipid, cholesterol and fatty acid. Currently, many organizations are conducting studies on the hemoglobin vesicle. The use of a hemoglobin vesicle entails advantages such as: 1) natural hemoglobin can be used as it is; 2) the side effects resulting from hemoglobin can be suppressed; 3) the viscosity, colloidal osmotic pressure and oxygen affinity can be adjusted to arbitrary values, respectively; and 4) the residence (retention) time in circulation system of the living body can be prolonged.

It is known that a heme (protoporphyrin IX), which is an oxygen bonding site of hemoglobin, loses its oxygen bonding capability when it escapes from globin. Thus, it has been well recognized that the stereoscopic frame constructed by globin chains plays a significant role and the hydrophobic field formed therein is important. Consequently, much effort has been dedicated for developing a system which can substitute for the functions of globin.

The present inventors studied various types of porphyrin derivatives and have succeeded in synthesizing a lipid heme (lipid-bonded heme): 5, 10, 15, 20-tetrakis [α, α, α, α-o-{2',2'-dimethyl-20'(2"-trimethylammonioethyl) phosphonatoxy eicosanamido}phenyl]porphynato-iron (II) and others, which have the capability of bonding with oxygen reversibly in aqueous systems. In a lipid heme vesicle produced by mixing the above lipid heme together with phospholipid, and then dispersing the resulting mixture in an aqueous phase, the lipid hemes are embedded in hydrophobic field of a phospholipid membrane and thus suspended and orientated in the membrane. In a lipid heme vesicle in an aqueous suspension system with a uniform particle size, it has been observed that reversible coordination of oxygen is possible as in the case of hemoglobin in a erythrocyte under physiological conditions. Thus, a red-color aqueous system having the same heme concentration as that of blood appeared as the first oxygen infusion manufactured by total synthesis (E. Hasegawa et al., Biochem. Biophys. Res. Commun. vol. 105, 1416 to 1419, 1982). Bioassay was also carried out extensively by administrating the lipid heme vesicle into animals. In particular, in the resuscitation test for a canine model of hemorrhagic shock, it was confirmed that the lipid heme had oxygen-carrying capability in accordance with the heme concentration. It was further confirmed that a lipid heme-triglyceride microsphere, prepared by covering the outer surface of an microsphere of a nutritional oil material (such as purified soybean oil or triglyceride) with a lipid heme, exhibits an oxygen carrying capability.

Further, another oxygen infusion agent was synthesized which contains 2-[8-{N-(2-methylimidazolyl)}octanolyloxymethyl]-5,10,15,20tetrakis [α, α, α, α-o-pivaloamido]phenylporphynato-iron (II) adsorbed in a hydrophobic pocket of human serum albumin or genetically engineered human albumin, the oxygen infusion agent being referred to as "albumin-heme", hereinafter. Further, it has been confirmed that the albumin-heme has an oxygen carrying capability (E. Tsuchida et al., Bioconjugate Chemistry, vol. 8, 534–538, 1997).

Thus, considering the current state of such oxygen infusions, one of the principal remaining issues is the preservation thereof.

Methods are known for preserving an oxygen infusion, namely, frozen storage and storage in the form of freeze-dried powder. However, the frozen material requires thawing, which is laborious. On the other hand, the freeze-dried powder requires much time for dissolution in aqueous solution, and further entails the problem of a complicated operation, such as removal of bubbles generated upon dissolution in the solution. Therefore, the frozen storage and freeze-dried powder storage methodologies are not preferred.

In addition, the qualities of oxygen infusions deteriorate with time due to the inherent characteristics of heme protein, and therefore it is difficult to preserve them in a stable condition. More specifically, hemoglobin, lipid heme and heme derivatives can reversibly bond with oxygen when the central iron of heme is a ferrous iron ($Fe_{2+}$), whereas when the ferrous iron is oxidized to a ferric iron ($Fe^{3+}$), oxygen binding capability is lost. Further, even a ferrous complex bound with oxygen is gradually oxidized automatically while releasing superoxide anion ($O_2^-$), and is finally converted to a ferric iron. Thus, the complex loses its oxygen binding capability (for example, hemoglobin becomes methemoglobin). Further, heme protein thus converted to a met-form can easily release free heme and free ferric iron, which is a concern causing adverse effects on the living body.

Even where preservation is effected in a refrigerator to suppress the above-described oxidation by lowering the reaction rate, the amount of ferric heme gradually increases. In order to solve this problem, a method is known for reducing ferric iron into ferrous iron by adding a methemoglobin-reducing enzyme system which exists in erythrocytes, or an enzyme which can scavenge active oxygen, such as catalase or superoxide dysmutase. Also known is a method of maintaining the ferrous iron by binding carbon monoxide (CO) with heme. The affinity of carbon monoxide to hemoglobin or a heme derivative is as high 200 times that of oxygen, and therefore it is possible to suppress the oxidation to ferric iron for an extremely long period of time.

However, the above-described method in which a methemoglobin-reducing enzyme system or an active oxygen scavenger enzyme is added to the oxygen infusion, entails such drawbacks that the enzymatic activity is lowered during a long period of time and thus the enzymes lose their reduction potential. On the other hand, an oxygen infusion which is preserved in a refrigerator under a carbon monoxide atmosphere can not be directly administered into a human body because a great amount of carbon monoxide contained in the oxygen infusion is extremely harmful, and the oxygen bonding potential of the infusion cannot be exhibited unless the carbon monoxides bound with the heme are removed. For this reason, such a transfusion cannot be given as it is to the human body. In addition, in refrigerator preservation after being converted into an oxy-type, the oxidation to a ferric iron gradually proceeds and eventually the oxygen carrying potential is lowered. The correlation between the oxygen partial pressure of ferrous hemoglobin and the oxidizing rate is well known, and further, it has been experimentally confirmed that the oxidation reaction does not proceed with deoxyhemoglobin (Sakai et al., Bull. Chem. Soc. Jpn., 1994, 1120–1125; Takeoka et al., Bioconjugate Chem., vol. 8, 539–544, 1997).

In addition, even if the oxidation reaction of hemoglobin and heme derivative can be suppressed, the preservation of the oxygen infusion entails another problem. That is, molecular assembly structures, such as a hemoglobin vesicle, a lipid heme vesicle and a lipid heme-triglyceride microsphere which form the environment of heme, are often unstable since these structures are constructed not with covalent bonds but through molecular interaction forces (such as hydrophobic interaction, electrostatic interaction and hydrogen bonds) acting between molecules of the components. As a result, when such an oxygen infusion is suspended in a saline solution and preserved in a refrigerator, the vesicles are fused with each other to form aggregates of the vesicle population, thereby varying the particle diameter thereof. Consequently, there has been a demand for stabilizing the molecular assembly structure of the vesicles. The following is an example of the conventionally known stabilization technique.

Specifically, it is known that a polymerizable phospholipid may be used as a membrane component of a hemoglobin vesicle or a lipid heme vesicle, and the polymerizable phospholipid is polymerized by γ-ray or ultraviolet ray irradiation to highly stabilize the structure of the vesicle. In utilizing this technique, it is possible to preserve the resultant suspension for a long time by rapidly freezing it with liquid nitrogen. Further, even if the freezing and thawing are repeated for 10 times, leakage of hemoglobin, change in the particle diameter or variation in association-dissociation curve of oxygen is not observed (Satoh et al., ASAIO Journal, vol. 38, M580 to M584, 1992). In addition, there can be obtained an extremely stable powder by adding a sugar, such as maltose or sucrose, to the above-described suspension system, followed by freeze-drying the system. For example, for hemoglobin vesicle, it was confirmed that an aqueous suspension of the resultant lyophilized powder showed no leakage of hemoglobin, and no variation in particle diameter thereof, from the physical property analysis carried out on a hemoglobin vesicle which was preserved for 20 weeks at a temperature of 4° C., followed by adding pure water thereto for re-constituting suspension thereof. This indicates that the hemoglobin vesicle is in substantially the same state as that before the lyophilization (Wang et al., Polymer Adv. Technol., vol. 3, 7–21, 1992).

On the other hand, there is a conventionally well known method of introducing a polyoxyethylene-linked lipid onto a surface of a phospholipid vesicle. However, the object of this method is to extend the inblood retention time of the vesicle, thereby efficiently transporting an anticancer agent encapsulated therein to a tumor tissue. This method has already undergone clinical trials and the safety of the method has been fully confirmed. Further, it has been empirically confirmed that the dynamics of the bloodstream can be improved by modifying the surface of a hemoglobin vesicle with polyoxyethylene, which can suppress the interaction between a hemoglobin vesicle and a plasma protein (Sasaki et al., Bioconjugate Chemistry, vol. 8, 23 to 30, 1997). However, it is not known to utilize the polyoxyethylene modification method for the preservation of oxygen infusions, and, as noted above, a need exists for preservation of oxygen infusions.

SUMMARY OF THE INVENTION

It is an object of the present invention to preserve oxygen infusions for a long period of time at room temperature.

It is also an object of the present invention to provide a method for preserving an oxygen infusion containing an aqueous suspension of molecular assemblies which contain hemoglobin or a heme derivative or heme compound, the method entailing the steps of:

a) modifying the molecular assemblies with polyoxyethylene; and b) converting the hemoglobin or the heme derivative or compound into a deoxy-type or deoxy-form by removing oxygen from the suspension.

It is, moreover, another object of the present invention is to provide a method of producing an oxygen infusion containing an aqueous suspension of molecular assemblies which contain hemoglobin or a heme derivative or heme compound, the method entailing the steps of:

a) preparing a suspension of the molecular assembly modified with polyoxyethylene and containing the hemoglobin or the heme derivative;

b) converting the hemoglobin or the heme derivative or compound into a deoxy-type or form by removing oxygen from the suspension; and c) packing the suspension containing the deoxy-type or form hemoglobin or heme derivative, in an oxygen-impermeable container which is filled with an inert gas.

BRIEF DESCRIPTION OF THE DRAWING

The drawing is a graph indicating the stability in preservation of a polyoxyethylene-modified deoxy-type or form hemoglobin vesicle.

DETAILED DESCRIPTION OF THE PREFERRED EMBODIMENTS

Various documents are cited in this specification, and although only the titles are cited here, the entire contents of each citation are incorporated by reference herein.

In the present invention, the term "molecular assembly" refers to an assembled structure constructed of molecules such as lipids and/or proteins, for example, not through covalent bonds but through interactions (such as hydrophobic interaction, electrostatic interaction and hydrogen bond) acting between the molecules in an aqueous medium. Typical examples of the molecular assembly are a vesicle or a liposome and a microsphere, and in a broader sense, cell membranes such as erythrocyte membranes are included in the category of the molecular assembly. Further, a hemoglobin vesicle, lipid heme vesicle and a lipid hemetriglyceride microsphere, as well, are typical examples of the vesicle made of molecular assemblies. Also, albumin-lipid heme is a molecular assembly. It should be noted that the albumin-heme, as already described, is one in which a heme derivative is adsorbed in a hydrophobic pocket of human serum albumin or genetically engineered human albumin. Here, in many cases, a hydrocarbon chain is added to the heme derivative, and this hydrocarbon chain exhibits a property as a lipid; therefore the albumin-heme is also called albumin-lipid heme.

In the specification, the term "heme derivative" or "heme compound" of the "hemoglobin or heme derivative" encompasses all of the Heme derivatives or compounds in which a porphyrin ring of heme is modified with a substituent and has a reversible oxygen-binding potential.

The term "aqueous medium" as used in the present specification includes water and all kinds of aqueous solutions which is physiologically acceptable, such as an electrolyte aqueous solution, a buffer solution, an aqueous protein solution, an aqueous lipid emulsion, blood plasma, a plasma expander (aqueous colloidal solution such as dextran, hydroxyethyl starch, gelatin or the like) and a combination of any of these.

The inert gas of the present invention means a chemically inert gas, which is, for example, a rare gas such as helium, argon or neon, or nitrogen. For economical reasons, nitrogen gas is preferable.

The following are detailed descriptions for practicing the present invention.

Saline suspensions of the following materials were prepared by the methods described in the respective documents, that is, hemoglobin vesicles (Sakai et al., Biotechnology Progress, vol. 12, 119–125, 1996), lipid heme vesicle (E. Hasegawa et al., Biochem. Biophys. Res. Commun., vol. 105, 1416–1419, 1982), lipid hemetriglyceride vesicle (E. Tsuchida et al., Chemistry Letters, vol. 1992, p1325–1328, 1992), and albumin heme (E. Tsuchida et al., Bioconjugate Chemistry, vol. 8, 534–538, 1997). With regard to these aqueous suspensions, it is confirmed that each suspension is in a state where the heme is of a ferrous iron. Then, the suspension is adjusted to have a predetermined components concentration (for example, hemoglobin concentration of 10 g/dL, heme concentration of 6.2 mM) and oxygen is removed from the suspension. The oxygen removing method operates in the following manner. That is, the suspension is exposed to an oxygen-free nitrogen gas or some other inert gas (such as of argon or helium), thereby evacuating oxygen dissolved in the suspension. As this operation is carried out, an oxy-type heme is converted into a deoxy-type or deoxy-form heme, to which oxygen is not bound. In practice, the following procedure can be taken. That is, the suspension is charged into a hermetically sealed container such as a glass bottle, through which oxygen cannot permeate, and the inert gas is bubbled within and evacuated from the container to strip the dissolved oxygen from the suspension. In this manner, oxygen remaining dissolved in the infusion can be removed.

The dissolved oxygen concentration can be determined using a known method of monitoring the oxygen partial pressure while immersing a Clark type oxygen electrode in the suspension, or a method of measuring, by gas chromatography, a gas phase collected from the container, or a method of calculating the ratio between the oxy-type and deoxy-type hemoglobins based on measurements of visible and near infrared spectral absorptions which is characteristic of hemoglobin or heme in the container. Each of thus obtained deoxy-type oxygen infusions can be preserved while being sealed from oxygen, thereby suppressing the oxidation of hemoglobin or heme, or the oxidation of some other components including lipid.

After the above-described oxygen removing operation, in order to further remove a trace amount of oxygen remaining in the solution, an appropriate amount of a thiol, such as homocysteine, acetylcysteine or glutathione, or a small amount of reductive reagent which reacts with oxygen, such as ascorbic acid and dithionite, may be dissolved into the vesicles or the suspension itself.

Each of the resulting deoxy-type or deoxy-form oxygen infusions obtained as described above is preserved while being isolated from oxygen. For example, it may be directly sealed in a glass bottle or in an aluminized polyethylene bag or container made of a material having an extremely low oxygen permeability, such as a polyvinylidene chlorides or ethylene-vinyl alcohol copolymers. Or each agent is sealed in a plastic bag, and the bag is further placed in a container through which oxygen does not permeate. The preservation temperature should be in a range of about −20° C. to 60° C., and more preferably, it should be preserved in a cool and dark place in a range of about 4 to 25° C. With the above-described procedure, it is possible to suppress the oxidation of hemoglobin or heme, or the oxidation of some other component such as lipid, due to oxygen.

In order to further improve the stability in preservation, it is preferable that, in addition to the above-described oxygen removal, polyoxyethylene should be linked to the surfaces of the molecular assembly particles in advance. Here, for example, in the case where the above-described molecular assembly is made of lipids as its structural components, it suffices if a suspension of a lipid having a polyoxyethylene molecule linked thereto (that is, polyoxyethylene lipid) is added at a temperature of about 4 to 60° C. The hydrophobic moiety of the polyoxyethylene lipid molecule is inserted into and fixed on a surface of the molecular assembly particles containing the lipids, while a hydrophilic polyoxyethylene chain extends into the water phase in an elongated state (Sakai et al., Bioconjugate Chemistry, vol. 8, 23–30, 1997). It should be noted that the incorporation of the polyoxyethylene lipid is faster as the reaction temperature is higher; however the procedure may be carried out at lower temperature. Meanwhile, in the case where a great amount of cholesterol is contained in the molecular assembly, although no definite phase transition temperature is not specified, the introduction of the polyoxyethylene lipid can be fully conducted even below a phase transition temperature of the phospholipids ingredient. The molecular weight of the polyoxyethylene chain of the polyoxyethylene lipid may be about 1,000 to 20,000 Daltons, which is sufficient. The incorporation amount is about 0.01 to 3 mol % with respect to the total amount of the lipids exposed on the outer surface of each particle, or more preferably, the incorporation amount should be about 0.05 to 0.3 mol %. Examples of the hydrophobic site of the polyoxyethylene lipid include an ethanolamine-type phospholipids, cholesterol, alkyl-chain-linked glutamic acid, and alkyl-chain-linked lysine. The type of bond between polyoxyethylene and a lipid moiety may be of, for example, an ester bond, urethane bond, amide bond or ether bond. When polyoxyethylene chains are introduced into the surface of each particle, a change in the particle diameter due to the aggregation and fusion of the particles during preservation can be suppressed. On the other hand, in the case of hemoglobin vesicles, it is possible to prevent the leakage of encapsulated elements including hemoglobin from the vesicles.

The effect of the present invention having the above-described structure is as follows. First, the present invention is designed to suppress the oxidation of hemoglobin or heme derivative in the oxygen infusion by removing oxygen. Due to the effect of the suppression of oxidation, the generation of superoxide anion or hydrogen peroxide can be prevented during preservation, and therefore the oxidation and denaturing of the molecular assemblies which carry hemoglobin or heme derivative. As a result, the physical stability of the molecular assembly particles is improved, and the aggregation of the particles and the change in the particle diameter can be prevented. Therefore, the preservation life of the oxygen infusion comprising molecular assembly particles can be prolonged.

Second, by introducing polyoxyethylene chain into the surfaces of molecular assembly particles of hemoglobin vesicles, lipid heme vesicles, lipid hemetriglyceride microspheres, etc., the molecular assembly particles can be further stabilized. In this manner, the change in the particle diameter due to the aggregation and fusion of the particles which may take place during preservation, or the leakage of encapsulated elements including hemoglobin from the particles can be effectively prevented. Therefore, the preservation stability of the oxygen infusion can be further improved.

Further, in accordance with the present invention, there is a relationship between the oxidation of heme iron from ferrous ion to ferric ion and the instability of the molecular assembly structure, which promote one another mutually. More specifically, superoxide anion ($O_2^-$) and hydrogen peroxide which are generated along the oxidation of heme iron, as well as ferri-hemoglobin thus created, serve to oxidize the structural components of the molecular assemblies, thereby promoting the destruction of the molecular assemblies. On the other hand, the destruction of the molecular assemblies can deteriorate the circumstances where heme irons exist, thereby promoting the oxidation of the heme. The present invention also focuses on this consideration and aims to suppress the oxidation of hemoglobin and a heme derivative, and to stabilize molecular assemblies serving as carriers for hemoglobin and the heme derivative, at the same time. In this manner, it becomes possible to store the oxygen infusion at room temperature.

It is also noted that the oxygen infusion which uses an albumin-heme is stable in the state of solution, and therefore a relatively high stability can be achieved even though the modification by polyoxyethylene is not employed. However, with the modification by polyoxyethylene, the stability is further improved. When this modification is combined with preservation in an oxygen-free state, the conversion of heme into a met-type can be prevented, and thus the preservation stability can be remarkably improved, as in the above-described case.

Thus, deoxygenated-type oxygen infusions can be preserved for a long term. Therefore, when the oxygen infusion is kept in stock regularly in sections of clinical facilities, ambulances and remote areas where no medical facilities are located, the oxygen infusion can be administered into the patient's body immediately when needed. The deoxy-type oxygen infusion, when exposed to the atmosphere, is bound with oxygen to become an oxy-type. On the other hand, even if the oxygen infusion is administered into a vein directly in the form of deoxy-type, it binds with oxygen immediately when it first passes the lung to become an oxy-type, and then releases oxygen in peripheries.

Reference will now be made to certain Examples which are provided solely for purposes of illustration and are not intended to be limitative.

EXAMPLE 1

Pyridoxal 5'-phospholic acid was added to a high-purity stroma-free carbonyl hemoglobin (HbCO) solution (40 g/dL) obtained by purification of human erythrocytes such that the amount of Pyridoxal 5'-phospholic acid was 3 times molar excess of that of hemoglobin. Then, homocysteine was further added to the mixture to achieve a concentration of 5 mM, and then pH of the resultant mixture was adjusted to 7.4 with use of 1M-$Na_2CO_3$. The obtained mixture was filtrated through FM Microfilter (a product of FUJI FILM) having a pore diameter of 0.22 µm using Remolino (a product of Millipore), and a stock hemoglobin solution was obtained. After that, a mixed lipid powder, Presone PPG-I (a mixture of phosphatidylcholine/cholesterol/phosphatidylglycerol) was added to the solution little by little until the lipid concentration became 4.5% by weight, and then the resultant mixture was stirred at a temperature of 4° C. overnight, thus obtaining hemoglobin-containing multi-layered vesicles. With an extrusion method, the diameter of particles and the total layers of these vesicles were controlled. Eventually, the filtration was carried out two times by using FM Microfilter (having a pore diameter of 0.22 $\mu$m). Thus obtained hemoglobin-containing vesicles were diluted with a physiological saline to form suspension, and then, the resultant suspension was subjected an ultracentrifugal separation (50,000 g, 40 min). After that, the supernatant hemoglobin solution was removed by suction, and then, the resultant hemoglobin vesicles are re-suspended in a physiological saline.

Then, a polyoxyethylene-linked lipid, N-(monomethoxypolyoxyethylenecarbamyl) distearoylphosphatidyl-ethanolamine, dissolved in a physiological saline (molecular weight of polyoxyethylene chain was 5300) was supplied dropwise to the above-prepared suspension, in an amount equivalent to 0.3 mol % of the lipids exposed on the outer surface of each vesicle. The resultant was stirred at 25° C. for two hours, and then at 4° C. overnight, thus modifying the surface of each hemoglobin vesicle with polyoxyethylene.

The hemoglobin vesicle suspension (0.5 g/dL, 200 mL) was put in a cylindrical flask, which in turn was loaded in a rotary evaporator, and thus the flask was rotated (56 rpm). Then, on a liquid membrane formed by this operation, visible light was irradiated using a halogen lamp (500 W) under an oxygen stream condition (1 L/min) for 3 minutes. In this manner, carbon monoxide-bound hemoglobin (HbCO) was converted into oxyhemoglobin (HbO$_2$) by way of ligand exchange. Thus obtained suspension was subjected to an ultracentrifugal separation so as to sediment hemoglobin vesicle particles, and then, physiological saline as the external aqueous phase was removed. Then, the resultant hemoglobin vesicles were resuspended by adding the phosphate buffered physiological saline to the particles. Thus obtained suspension was filtrated with a 0.45 $\mu$m-filter, Dismic-25 (a product of ADVANTEC) after setting the hemoglobin concentration to 10 g/dL. In this manner, polyoxyethylene-modified hemoglobin vesicles were obtained.

30 mL of the suspension of the polyoxyethylene-modified hemoglobin vesicles described above was received in a 100 mL vial and sealed therein. Then, a nitrogen gas, which was filtered through a sterile disk filter and saturated with water vapor, was introduced to the vial and bubbled within the vesicle suspension in order to remove the dissolved oxygen. The oxygen partial pressure within the system was monitored with use of a Clark type oxygen electrode (Oxygen Partial Pressure Measuring Apparatus,=Po$_2$–100, Inter Medical), and it was observed that the oxygen partial pressure was decreased to 1 Torr. Thus, it was determined that oxyhemoglobin was converted into deoxyhemoglobin by the procedure described above.

The obtained oxygen infusion according to the present invention was subjected to preservation test. Preservation conditions used here were preservation in a refrigerator (4° C.), room temperature preservation (23° C.), and preservation in an incubator (40° C.). With regard to samples for these conditions, the following measurements were carried out for one year and the measured results were compared with the sample before these preservations.

(1) 30 mL of each sample was diluted by 100 folds with physiological saline and then each dilution was subjected to measurement in terms of ultraviolet visible absorption spectrum from 300 to 900 nm by using a 1-mm cuvette at room temperature. As compared with the samples before the preservation, the presence/absence of development of a new absorption peak, the shift of the wavelength where a Q-band peak and the like were studied.

(2) The presence/absence of a sediment formation in a respective sample was visually monitored with naked eyes. 30 mL of each sample was diluted by 10 folds with physiological saline, and then, subjected to measurement in terms of absorbance at 900 nm by using a 1-mm cuvette at room temperature. The absorbance of the physiological saline at 900 nm was subtracted as a reference from the measured value, and thus obtained value was taken as the turbidity of the respective sample.

(3) About 0.2 mL of each sample was diluted with a phosphate buffered saline (PBS) by 200 folds, and then, subjected to ultracentrifugal separation (100,000 g, 15 min). After that, the supernatant liquid of each sample was examined for quantitative analysis of hemoglobin, and thus the presence/absence of hemolysis was determined.

(4) The distribution of the particle diameters was measured by a dynamic light-scattering photometry at a temperature of 25° C. using Sub-micron Particle Analyzer Model N4-SD (Coulter Corporate Communications).

(5) An oxygen association/dissociation curve was measured with use of Hemox-Analyzer (TCS Model Products Co.), and from the analysis, the oxygen affinity ($P_{50}$), the oxygen-transporting efficiency (OTE) and the Hill number were calculated.

(6) In order to study the decomposition of the lipids, about 0.2 mL of each sample was lyophilized and the lipids were extracted using CHCl$_3$. The measurement was conducted by two-dimensional thin layer chromatography (silica gel plate) using, as developing mediums, chloroform/methanol/28% ammonia=13/7/1 (in volume ratio) and chloroform/acetone/methanol/acetic acid/water=10/4/2/2/1 (in volume ratio).

(7) About 0.2 mL of each sample was lyophilized and the membrane components were extracted with about 1 mL of CDCl$_3$, followed by filtration with a filter. Then, the resultant sample was measured in terms of $^1$H-NMR spectrum (JNM-LA500, Nihon Denshi). On the other hand, in order to remove polyoxyethylene chains dissociated into the external aqueous phase, about 0.2 mL of each sample was diluted with PBS by about 200 folds and the supernatant liquid was removed by an ultracentrifugal separation (100,000 g, 15 min). After the sediments was re-suspended with PBS, the resultant was freeze-dried, and then the membrane components were extracted using about 1 mL of CDCl$_3$, followed by a filtration with a filter. Then, the resultant was measured in terms of $^1$H-NMR spectrum. The peak (B) which is assigned to the methylene protons of polyoxyethylene chain in polyoxyethylene lipid appeared at $\delta$:3.63 ppm, whereas the peak (A) which is assigned to choline methyl proton of phosphatidyicholine appeared at $\delta$:3.39 ppm. Supposing that the ratio between the number of protons in the peak (A) to that in the peak (B) is equal to the integral ratio of B/A, the incorporation ratio of polyoxyethylene chains was calculated by way of the following formula:

$$B/A(after) \div B/A(stock) \times 100$$

wherein
B/A(after) is the Integral ratio B/A after removal of external water phase; and
B/A(stock) is the integral ratio B/A of stock solution.

The drawing shows changes of various physical property values of hemoglobin vesicle suspension during the time course of the preservation. In any of the samples, appearance of a new peak at 630 nm characteristic to the methemoglobin in the ultraviolet visible absorption spectrum, a change in absorbance of Q-band or Soret band, or shift of wavelength was not observed during a preservation period for 1 year. Further, no hemolysis was confirmed or no dissociated fatty acid was observed in the two-dimensional thin layer chromatography. In any of the samples, after six months of preservation, no sediment due to aggregation was observed, and the particle diameters or turbidity was not substantially changed. Further, after preserving for six months at 40° C., the polyoxyethylene chain incorporation was maintained only to a decrease of about 7% as compared to that before the preservation. The decrease of $P_{50}$ was as small as 5.5 Torr as compared to that before the preservation, even after preserving for six months at 40° C. With such a small degree of decrement, it was determined that the oxygen transporting function of hemoglobin vesicle was not affected. However, in the case of a preservation of one year at 40° C., a decomposition of a lipid and a decrease of $P_{50}$ to 43 Torr were observed. In each of the samples, the initial rate of conversion into methemoglobin after preservation was decreased, and became less than 1% after one month of preservation. This is because that the oxidized methemoglobin was reduced by homocysteine. From the above observations, it was determined that the hemoglobin vesicle whose surface was modified with polyoxyethylene chain can be preserved for six months at 40° C., or one year at 23° C., on a shelf under a nitrogen atmosphere, and thus exhibit no loss of oxygen transport function.

EXAMPLE 2

A suspension of hemoglobin vesicles which are not modified with polyoxyethylene was prepared in a similar manner to that of Example 1, and the suspension was received in a vial and sealed therein. Then, a nitrogen gas, which was filtered with a sterile disk filter and saturated with water vapor, was introduced to the vial and was bubbled within the vesicle suspension in order to remove the dissolved oxygen completely. The oxygen partial pressure within the system was monitored by using Oxygen Partial Pressure Measuring Apparatus ($Po_2$–100, a product of Inter Medicals), and it was observed that the oxygen partial pressure was decreased to 2 Torr. Thus, it was determined that with the above-described procedure, oxyhemoglobin was converted into deoxyhemoglobin.

The obtained oxygen infusion was subjected to preservation test. Preservation conditions used entailed preservation in a refrigerator (4° C.), room temperature preservation (23° C.), and preservation in an incubator (40° C.). The following measurements were carried out for the samples for six months and the measured results were compared with the sample before these preservations. That is, the presence/absence of a sediment formation in the sample in each case was visually observed with naked eyes. 30 mL of each sample was diluted by 10 folds with physiological saline, and then, subjected to measurement in terms of absorbance at 900 nm using a 1-mm cuvette room temperature. The absorbance of the physiological saline at 900 nm was subtracted as a reference from the measured value, and thus obtained value was taken as the turbidity of the respective sample. The measurement of the distribution of particle diameters was conducted by a dynamic light-scattering method using Sub-micron Particle Analyzer Model N4 SD (Coulter Corporate Communications) at a temperature of 25° C.

An increase in the methemoglobin content was not at all observed, and it became substantially constant after one month of preservation. With regard to the increase in the particle diameter, it increased about 8% after one week of preservation and a small amount of sediment formed by aggregation was observed. However, each sample was still in a usable condition. By contrast, in the case where oxygen was not removed, sediment was formed as early as one week of preservation to such a degree that the infusion cannot be used. Therefore, it can be understood that the removal of oxygen contributed also to the stabilization of hemoglobin vesicles.

However, from the comparison with the results of Example 1, it was found that the particle diameter drastically increased during the preservation in each sample. Such results indicate that the modification of the surfaces of hemoglobin vesicles with polyoxyethylene, and the preservation of the agent under an oxygen-free condition, interact synergistically with each other, thereby achieving a further significant preservation stability.

EXAMPLE 3

A polyoxyethylene-modified hemoglobin vesicle suspension (molecular weight of polyoxyethylene: 2000) was prepared in a similar manner to that of Example 1. The obtained deoxy-form was transferred into an aluminum bag (Aluminized polyethylene bag, a product of GL Sciences, Inc.) under a nitrogen atmosphere, in order to isolate it from oxygen. The obtained infusion was preserved under conditions of preservation in a refrigerator (4° C.), room temperature preservation (23° C.), and preservation in an incubator (40° C.). With regard to each sample for these conditions, the same measurements as those of Example 1 were conducted for one year. The results obtained here were similar to those of Example 1.

EXAMPLE 4

A polyoxyethylene-modified hemoglobin vesicle suspension (50 mL) was prepared in a similar manner to the preparation method employed in Example 1 except that homocysteine used in Example 1 was replaced by glutathione and the molecular weight of polyoxyethylene chain of the polyoxyethylene lipid was adjusted to 10,000. Thus prepared suspension was received in a cylindrical flask (2L), which was loaded in a rotary evaporator and rotated (60 rpm), thus creating a liquid membrane of the hemoglobin vesicle suspension. A nitrogen gas was put through (1.0 L/min) the liquid membrane in order to remove oxygen therefrom. Then, it was confirmed using a near-infrared region noninvasive oxygen monitor (Model OM-200, a product of Shimazu Corporation) that 98% or more of the entire hemoglobin was deoxy hemoglobin. Thus obtained resultant was sealed in a refrigeration pack, Cryocyte (a product of Baxter) and further sealed in a aluminum can in order to block off the penetration of oxygen. Thus obtained infusions were subjected to preservation test, in which they were preserved under conditions of preservation in a refrigerator (4° C.), room temperature preservation (23° C.), and preservation in an incubator (40° C.). With regard to each sample for these conditions, the same measurements as those of Example 1 were conducted for one year. The results obtained here were similar to those of Example 1.

EXAMPLE 5

A lipid heme vesicle suspension was made of 5, 10, 15, 20-tetrakis [α, α, α, α-o-{2', 2'-dimethyl-20'(2"-trimethylammonioethyl)phosphonatoxyeicosanamido}-phenyl]porphynato-iron(II) (lipid heme)/1-stearylimidazole/dipalmitoyl phosphatidyl choline/cholesterol/ polyoxyethylene-conjugated phospholipid which is—(monomethoxypolyoxyethylenecarbamyl) diphosphatidyl ethanolamine, in a molar ratio of 1/3/40/20/2.5. The average molecular weight of the polyoxyethylene chains was adjusted to 5000. To the suspension, physiological saline was added to prepare a solution having a lipid heme concentration of 5 mM. The solution was subjected to the extrusion method described in Example 1 so as to control the particle diameter, and then sealed into a glass container with addition of 6 mM of ascorbic acid. Then, a nitrogen gas was put through the solution by the same method as in Example 1. As a result, ferric iron hemes were all reduced to ferrous iron hemes and the oxygen partial pressure was reduced to low as 3 Torr; therefore substantially all of the vesicles in the container became deoxy-type lipid heme vesicles. Thus obtained infusion was preserved at room temperature for three months, and the analysis thereof did not show any indication of increase in the amount of ferric iron heme. Further, the particle diameter was 105±21 nm before the preservation, whereas after the preservation, it was 107±28 nm, exhibiting no substantial change. A significant increase in turbidity was not observed.

EXAMPLE 6

For the preparation of a lipid heme-triglyceride microsphere suspension, a soybean oil ([soybean oil]/[heme]=a ratio of 2 to 4 by weight) was added to 5, 10, 15, 20-tetrakis [α, α, α, α-o-{2',2'-dimethyl-20'(2"trimethylammohioethyl) phosphonatoxyeicosanamido}-phenyl] porphynato-iron(II) (lipid heme)/1-stearylimidazole (at a ratio in molar of 1/2.5), and further a 2%-glyceline aqueous solution was added thereto. Then, the mixture was subjected to supersonic agitation in a water bath under a nitrogen atmosphere, thus obtaining the suspension. To the suspension, a polyoxyethylene-conjugated lipid having an average molecular weight of 2000, N-(monomethoxypolyoxyethylenecarbanyl) dipalmitoylphosphatidyl ethanolamine, was added at a ratio of 0.02 mol % with respect to the lipid heme, so as to modify the lipid heme-triglyceride microsphere with polyoxyethylene. 180 mL of thus obtained suspension was then sealed into a 200 mL-glass container with a slightly excessive amount of ascorbic acid added therein. Then, the bubbling with a nitrogen gas was performed by the same method as in Example 1, and thus the oxygen partial pressure was reduced to low as 2 Torr. Thus, deoxy-type lipid heme-triglyceride microspheres were obtained. The resultant suspension was preserved at room temperature for four months, and the analysis thereof did not show any indication of increase in the amount of ferric iron heme. Further, the particle diameter was 85±25 nm before the preservation, whereas after the preservation, it was 86±28 nm, exhibiting no substantial change.

EXAMPLE 7

Albumin-heme was prepared from a heme derivative, i.e., (2-[8-{N-(2-methylimidazolyl)}octanoyloxymethyl]-5,10,1 S, 20-tetrakis (α, α, α, α-o pivalamido) phenylporphynato-iron(II)), and human serum albumin by the method described in the aforementioned document (E. Tsuchida et al., Bioconjugate Chemistry, vol. 8, 534 538, 1997), the content of which is incorporated herein by reference. After confirming that the ferric iron hemes are bound with oxygen, the resultant albumin-heme solution was sealed into a glass container. Then, a nitrogen gas was put through the solution by the same method as in Example 1, and thus the oxygen partial pressure was reduced to low as 3 Torr. Thus, the deoxy-type albumin-hemes were obtained. The resultant albumin-heme solution was preserved at 20° C. for five months, and the analysis thereof did not show any indication of increase in the amount of ferric iron heme. Further, an increase in the amount of insoluble matter was not observed.

COMPARATIVE EXAMPLE 1

A polyoxyethylene-modified hemoglobin vesicle suspension (50 mL) was prepared in a similar manner to the preparation method employed in Example 1. The oxygen partial pressure was adjusted to the same as that of atmosphere, that is, 149 Torr, under a sterile atmosphere. The obtained suspension was sealed in a vial, which was preserved in a incubator (40° C.) without removing oxygen therefrom, and therefore, in the form of oxyhemoglobin. During the preservation, the rate of conversion into methemoglobin was measured from the ultraviolet visible light absorption spectrum at 1, 4 and 24 hours later. As the time elapsed during the preservation, the methemoglobin content was increased from 2.7%, which was the value before the preservation, to 5% after one hour of preservation, to 12% after four hours of preservation, and to 36% after 24 hours of preservation.

These results indicate that even a polyoxyethylene-modified hemoglobin vesicle suspension exhibits a significant increase in the amount of methemoglobin when oxygen is not removed. Therefore, in that case, a preservation stability similar to that of the present invention cannot be obtained.

Having described the present invention, it will now be evident to one of ordinary skill in the art that many changes and modifications may be made to the above-described embodiments without departing from the spirit and the scope of the present invention.

What is claimed is:

1. A method for preserving an oxygen infusion comprising an aqueous suspension of molecular assemblies which contain hemoglobin or a heme compound, said method comprising the steps of:
   a) modifying the molecular assemblies with polyoxyethylene; and
   b) converting the hemoglobin or the heme compound into a deoxy-form by removing oxygen from the suspension.

2. The method of claim 1, wherein the molecular assemblies are selected from the group consisting of cell membranes, hemoglobin vesicle, lipid heme vesicle, lipid heme-triglyceride microsphere and albumin-lipid heme.

3. The method of claim 1, wherein the removal of oxygen is performed by gas exchange with an inert gas.

4. The method of claim 1, further comprising:
   storing said suspension in an oxygen-impermeable container filled with an inert gas.

5. The method of claim 1, wherein the suspension contains a physiologically acceptable reducing agent.

6. The method of claim 1, wherein the heme compound comprises a porphyrin ring having a substituent, said compound having reversible oxygen-binding potential.

7. The method of claim 1, wherein the molecular assemblies are modified by fixing the polyoxyethylene onto surfaces thereof.

8. The method of claim 7, wherein said polyoxyethylene has a molecular weight of about 1,000 to 20,000 Daltons.

9. The method of claim 7, wherein the molecular assemblies comprise lipid and said polyoxyethylene is present in an amount of about 0.01 to 3 mol % with respect to a total amount of lipid exposed on an outer surface of each particle of the molecular assemblies.

10. The method of claim 7, wherein the polyoxyethylene is fixed into the surface of the molecular assemblies by a hydrophobic moiety of the components of molecular assembly.

11. The method of claim 10, wherein the hydrophobic moiety comprises at least one amphipathic molecule selected from the group consisting of ethanolamine phospholipid, cholesterol, alkyl-chain-linked glutamic acid and alkyl-chain-linked lysine.

12. The method of claim 11, wherein the polyoxyethylene is N-(monomethoxypolyoxyethylene carbamyl)distearyl phosphatidyl-ethanolamine.

13. The method of claim 1, wherein said oxygen infusion exhibits no loss of oxygen transport function after storage at 40° C. for six months.

14. The method of claim 1, which further comprises after step b), storing said oxygen infusion under nitrogen.

15. The method of claim 14, wherein said oxygen infusion exhibits no loss of oxygen transport function after storage at 23° C. under nitrogen for one year.

16. A method of producing an oxygen infusion comprising an aqueous suspension of molecular assemblies which contain hemoglobin or a heme compound, said method comprising the steps of:
    a) preparing a suspension of the molecular assembly containing the hemoglobin or the heme compound, the molecular assembly being modified with polyoxyethylene;
    b) making the hemoglobin or the heme compound into a deoxy-form by removing oxygen from the suspension; and
    c) packing the suspension containing the deoxy-form hemoglobin or heme compound, in an oxygen-impermeable container which is filled with an inert gas.

17. An oxygen infusion, comprising a suspension of molecular assemblies comprising hemoglobin or a heme compound, the assemblies being modified with polyoxyethylene; said hemoglobin or heme compound being in a deoxy-form.

18. The oxygen infusion of claim 17, wherein said molecular assemblies are modified by having said polyoxyethylene fixed onto surfaces thereof.

19. The oxygen infusion of claim 18, wherein the molecular assemblies comprises lipid and said polyoxyethylene is present in an amount of about 0.01 to 3 mol % with respect to a total amount of lipid exposed on an outer surface of each particle of the molecular assemblies.

20. The oxygen infusion of claim 17, wherein said polyoxyethylene has a molecular weight of about 1,000 to 20,000 Daltons.

21. The oxygen infusion of claim 17, wherein the molecular assemblies are cell membranes.

22. The oxygen infusion of claim 17, wherein the molecular assemblies are hemoglobin vesicles.

23. The oxygen infusion of claim 17, wherein the molecular assemblies are lipid heme vesicles.

24. The oxygen infusion of claim 17, wherein the molecular assemblies are lipid heme-triglyceride microspheres.

25. The oxygen infusion of claim 17, wherein the molecular assemblies are albumin-lipid heme.

26. The oxygen infusion of claim 17, which is stored in a container.

27. The oxygen infusion of claim 26, wherein the container is a bottle.

28. The oxygen infusion of claim 26, which is stored under an inert gas atmosphere.

* * * * *